United States Patent [19]

Fink et al.

[11] Patent Number: 5,786,893
[45] Date of Patent: Jul. 28, 1998

[54] RAMAN SPECTROMETER

[75] Inventors: Manfred F. Fink; John C. Robinson; Walter F. Buell, all of Austin, Tex.

[73] Assignee: Board of Regents, The University of Texas System, Austin, Tex.

[21] Appl. No.: 312,439

[22] Filed: Sep. 26, 1994

Related U.S. Application Data

[63] Continuation of Ser. No. 48,020, Apr. 15, 1993, abandoned.

[51] Int. Cl.[6] .............................. G01N 21/65; G02B 5/22
[52] U.S. Cl. .............................. 356/301; 359/885; 372/32
[58] Field of Search ........................... 356/301; 359/885, 359/886; 372/32

[56] References Cited

U.S. PATENT DOCUMENTS

| | | | |
|---|---|---|---|
| 3,414,354 | 12/1968 | Siegler | 356/301 |
| 4,823,354 | 4/1989 | Znotins et al. | 372/32 X |
| 4,859,028 | 8/1989 | Moore et al. | 359/885 X |
| 4,862,101 | 8/1989 | Emmons | 359/886 X |
| 4,953,961 | 9/1990 | Ubhayakar | |
| 4,953,976 | 9/1990 | Adler-Golden et al. | 356/301 |
| 4,986,656 | 1/1991 | Sweeney et al. | 356/301 X |
| 5,153,670 | 10/1992 | Jansson et al. | 356/301 |
| 5,247,343 | 9/1993 | Burch | 356/301 X |

OTHER PUBLICATIONS

Letokhov "Laser Spectroscopy; 5. Raman Spectroscopy" Optics & Laser Technology, Jun. 1978, pp. 129–137.

Yu, J. et al., "Narrowband Frequency Control of an Injection-Locked Diode-Laser Battery," *J. Phys. III France*, 2:1615–1622, 1992, published in Europe.

Gregonis, D. et al., "A Commercial Anesthetic—Respiratory Gas Monitor Utilizing Human Spectroscopy," *SPIE*, 1336:247–255, 1990, published in USA.

Nibler, Joseph W., "Coherent Raman Spectroscopy: Techniques and Recent Applications," *Applied Laser Spectroscopy*, 313–328, 1990, published in USA.

Robinson, J.C. et al., "New Vapor Phase Spontaneous Raman Spectrometer," *Rev. Sci. Instrum.*, 63(6):3280–3284, 1992, published in USA.

Wang, W. et al., "Coherent Addition of Injection-Locked High-Power AlGaAs Diode Lasers," *Optics Letters*, 17(22):1593–1595, 1992, published in USA.

Keller, Richard A., and Nogar, Nicholas S., "Gasdynamic Focusing for Sample Concentration in Ultrasensitive Analysis," *Applied Optics*, 23(13):2146–2151, 1984, published in USA.

Muenchausen, Ross E. et al., "Gasdynamic Focusing in an Underexpanded Jet," *Applied Optics*, 28(15):3220–3225, 1989, published in USA.

Robinson, J.C. et al., "A New Vapor Phase Spontaneous Raman Spectrometer," *Proceedings of the Twelfth International Conference on Raman Spectroscopy*, Abstract A-974, 1990, place of publication unknown.

(List continued on next page.)

*Primary Examiner*—Vincent P. McGraw
*Attorney, Agent, or Firm*—Arnold, White & Durkee

[57] ABSTRACT

An improved Raman spectrometer is provided, having, in a preferred embodiment, a light source comprising an injection-locked laser diode array, a multipass cell to multiply the intensity of the light source, a dynamic gas sample focusing system, and an atomic vapor filter to remove the Rayleigh scattered light. The laser diode arrays are tuned to match an absorption band of the atomic vapor filter. The Raman scattered light passes virtually unattenuated through the filter to be recorded by a Fourier transform spectrometer or other spectrometer. This invention permits higher sensitivity and resolution than prior art Raman spectrometers, in particular permitting identification and measurement of Raman emissions that occur at low wave numbers. The light source of this invention can also be used in conjunction with optical notch filters and photodetectors to permit detection and measurement of preselected species in a sample.

32 Claims, 10 Drawing Sheets

OTHER PUBLICATIONS

Robinson, J.C. et al., "A New Spectrometer for Vapor Phase Spontaneous Raman Scattering, 'The Announcer'", *American Association of Physics Teachers*, 20(4), 1990. Abstract only, published in USA.

Robinson, John Charles, "A New Spectrometer for Vapor Phase Spontaneous Raman Scattering," *Graduate Thesis, The University of Texas*, Dec., 1991, pp. i–vi, printed in USA.

Robinson, J.C. et al., "A New Vapor Phase Spontaneous Raman Spectrometer," *Proceedings of the Thirteenth International Conference on Raman Spectroscopy*, 1992, place of publication unknown.

Kiefer, W., and Bernstein, H.J., "The Vapor–Phase Raman Spectra and the Ring–Puckering Vibration of Some Deuterated Analogs of Trimethylene Oxide," *J. Mol. Spectrosc.*, 43:393–400, 1972, published in USA.

Mazur, Eric, "Computer–Controlled Raman Spectrometer for Time–Resolved Measurements in Low–Pressure Gaseous Samples," *Rev. Sci. Instrum.*, 57(10):2507–2511, 1986, published in USA.

Hall, J.L. and Lee, S.A., "Interferometric Real–Time Display of CW Dye Laser Wavelength with Sub–Doppler Accuracy," *Applied Physics Letters*, 29(6):367–369, 1976, published in USA.

Spectra Diode Labs, 1991 Product Catalog, pp. 4–8 and 22–26, published in USA.

Author unknown, "Improved Raman–Emission Detector," NASA Tech Briefs, 16(8):41–42, 1992, published in USA.

Author unknown, "Hole Burning and Saturation Spectroscopy," Chapter 30, 1171–1212, name and place of publication unknown.

Hendra, Patrick et al., *Fourier Transform Raman Spectroscopy. Instrumentation and Chemical Applications.*, Ellis Horwood Series in Analytical Chemistry, Ellis Horwood, publisher, chapters 1–5, 12 and appendix, 1991, published in USA.

RAMAN SPECTROMETER

This application is a continuation of application Ser. No. 08/048,020, filed Apr. 15, 1993, now abandoned.

BACKGROUND

This invention relates to advances in analytical spectroscopy, in particular Raman spectroscopy. An improved Raman cell, light source, filtering system, and sample handling system are disclosed. The cell enhances the incident light generated by laser diode arrays, and the filter system prevents substantially all light of the source frequency from entering the spectrometer, but does not significantly attenuate other frequencies, even those quite close to the source frequency.

The precise knowledge of the composition of gases or other samples, either in the environment or during chemical processes, is of great significance in industry, medicine, and for environmental protection. Some analytical instruments are already available to achieve reliable and sensitive measurements for individual compounds. The analysis they perform works reasonably well for particular known compounds to be traced, even when their concentration is relatively low. In the percent to part per million (ppm) range, a spectroscopic technique can often be developed which will master identifying a particular compound. If the sensitivity has to be raised to the part per trillion level or further, the available instrumentation is essentially limited to mass spectrometric evaluations.

When making high precision spectrometric measurements it is generally necessary to use a tandem of three mass spectrometers in order to avoid interferences This will achieve the required sensitivity, but the complexity of the facilities requires constant calibrations to obtain accurate quantitative results.

Prior spectroscopic techniques are generally unable to continuously analyze multicomponent gases in real time with adequate sensitivity and accuracy. As interferences between compounds have to be considered, the dynamic range becomes limited and the absolute scales are lost. This makes measurements with presently known equipment questionable in this application.

Since we are interested in the detection and measurement of a large variety of compounds, all discussions herein are directed to the spontaneous Raman process. This is in contrast to resonance and stimulated Raman scattering, which are much more sensitive, but which require a specially tailored laser light source for each molecule to be detected. (Although features and aspects of the present invention may be applicable to resonant and stimulated Raman measurements as well.)

Many aspects of Raman spectroscopy are described in the first five chapters of Hendra, Jones and Warnes, *Fourier Transform Raman Spectroscopy*, (Ellis Horwood, 1991). During the spontaneous Raman process, an incident laser photon is absorbed by a target molecule, exciting the molecule into a state that is the superposition of all levels accessible from the initial state by dipole allowed transitions. All levels contribute only by the long ranged tail of their eigenstate wave functions to form this state. The closest lying state contributes most to the superposition. After less than $10^{-14}$ second, the excited state relaxes by the emission of a new photon. The energy of the emitted or scattered photons can be ordered into three groups.

"Rayleigh" scattering occurs when the incident and scattered photon have the same energy. This type of scattering is by far the strongest; it is also called "elastic scattering." After Rayleigh scattering, the molecule will return to the state it started from. Rayleigh scattered light has the same frequency as does the incident laser light. A major problem in Raman spectroscopy is elimination of the effects of Rayleigh scattering, which dominate the much weaker Raman scattering that contains all relevant information.

"Stokes" emissions have lower energies (lower frequencies) than do the incident laser photons. They occur when a molecule absorbs incident laser energy and relaxes into an excited rotational and/or vibrational state. Each molecular species will generate a set of characteristic Stokes lines whose intensities are proportional to the density of the species in the sample.

Finally, "anti-Stokes" emissions have higher frequencies than do the incident laser photons. Anti-Stokes emissions occur only when the photon encounters a molecule which, for instance, is initially in a rotational and/or vibrationally excited state due to its temperature. When the virtual state decays into a molecular state that is of lower energy than the initial state, the photon will be emitted with the energy of the incident photon plus the difference in energy between the molecule's original state and the molecule's final state. Like Stokes emissions, anti-Stokes emissions provide a quantitative fingerprint for the molecule involved in the scattering process. This part of the spectrum is seldom used for analytical purposes since the spectral features are weaker and molecular temperature adds an unnecessary variable. If, however, the temperature is the quantity to be determined, this part of the spectrum can reveal the internal temperature of each compound and the equilibrium condition in the gas sample.

The Stokes and anti-Stokes emissions are collectively referred to as "Raman" emissions. Since the frequency of the Stokes (and anti-Stokes) scattered light is typically far off the resonance of any component in the gas sample, fluorescence at frequencies of interest is minimal. The sample is optically thin and will not alter the intensities of the Stokes emissions (no primary or secondary extinctions), in stark contrast to infrared spectroscopy.

FIG. 1 illustrates a prior art generic Raman spectrometer. The sample to be studied is placed in gas cell 10 and illuminated by laser beam 12 which is emitted from laser 14. Suitable optical elements, such as mirror 16 may be used to focus and direct the laser beam 12. Light emitted from the illuminated sample in gas cell 10 is collected and concentrated by optics which may include collecting mirror 18 and lens 20. These collected emissions may be passed through filter 22 to eliminate light having undesirable wavelengths. The collected emissions are then conducted into triple spectrometer 24 by suitable optical elements which may include lens 26. Detection means, such as optical multichannel analyzer (OMA) 28 receive and record the output from triple spectrometer 24.

FIG. 2 shows a more sophisticated prior art Raman spectrometer than that shown in FIG. 1. See J. C. Robinson, et al., *Rev. Sci. Instr.*, Vol. 63, p. 3280–3284 (1991). In FIG. 2, laser 30 produces a beam 32 which is focused and directed by suitable optical elements such as mirror 34 and lens 36 into vacuum chamber 38. Once inside vacuum chamber 38, laser beam 32 is reflected between the two mirrors 40, 42 of a multi-pass cell, so that a cross-over is generated that enhances the laser power density by several orders of magnitude. In the case of a gas sample to be analyzed with this Raman spectrometer, the sample is introduced at the common focal region of mirrors 40 and 42 of the multi-pass cell. Light emitted from the sample that is irradiated by the concentrated laser beam are collected by optical elements such as mirror 46 and lens 48 and directed out of vacuum chamber 38 toward spectrometer 50. Additional optical elements such as dove prism 52 and lens 54 may be employed to condition and direct the collected emissions into the entrance slit of spectrometer 50. Reference laser 56 is commonly used to inject a light beam into spectrometer 50 for alignment purposes. A detector, such as charge coupled device 58, receives the output of spectrometer 50 and provides an input into recording or evaluating device such as computer 60.

There are two traditional methods known in the art to remove the dominating Rayleigh component from the collected emissions. The more expensive approach is the use of a triple monochromator, which consists of two low resolution units with subtractive dispersion, so that all stray light, anti-Stokes and Rayleigh scattered light can be removed very effectively. The remaining Stokes light may then be spectrally dispersed and the spectrum will be recorded with an optical multichannel analyzer (OMA). To gain the highest sensitivity, the least crosstalk between channels and the smallest dark current, charge-coupled device (CCD) technology is also used to detect the spectral signal. The primary disadvantages of this approach are the significant loss of intensity due to the many mirrors and gratings the light has to reflect from to reach the detector, and the expense of providing the triple monochromator. Therefore, it has become common for commercial Raman units to use stacks of edge filters to suppress light at the frequency of the source laser. In order to remove the Rayleigh component with such filters, up to 300 $cm^{-1}$ of the low end of the Stokes spectrum must be sacrificed. With appropriate filtering, only one good spectrometer is then needed to provide spectral dispersion, combined with an OMA for recording, but the low end of the spectrum is lost. The dispersive unit and the OMA may be replaced by a non-dispersive Fourier transform spectrometer equipped with a sensitive photomultiplier.

FIG. 7 shows a calculated quantitative example of a Raman spectrum of a hypothetical gas mixture. The resolution is assumed to be 10 $cm^{-1}$. This represents a realistic value for a standard grating spectrometer. The intensities are displayed on a natural logarithm scale. The strongest compounds are $N_2$ (77%) and $O_2$ (10%). The lone central line of these two molecules is the Q-branch where the rotational quantum number has not changed in the Raman process ($\Delta J=0$). The spectra at each side of the central lines are caused by $\Delta J$ of ±2 (S and O branches) transitions, and their intensity distributions are given by the occupation probabilities according to the Boltzmann distribution and the degeneracies of the J states. The remaining concentrations of the other molecules are given in Table 1.

TABLE 1

| Hypothetical Gas Mixture | |
|---|---|
| Molecular Species | Percentage |
| $N_2$ | 77 |
| $O_2$ | 10 |
| $CO_2$ | 4 |
| $H_2O$ | 3 |
| $N_2O$ | 3 |
| NO | 1 |
| CO | 1 |
| $O_3$ | ½ |
| $SO_2$ | ½ |

TABLE 1-continued

| Hypothetical Gas Mixture | |
|---|---|
| Molecular Species | Percentage |
| $NO_2$ | ½ |
| $H_2S$ | ½ |
| HCl | ½ |
| $C_2H_4$ | ½ |
| $C_6H_6$ | ½ |
| | 100% |

Note in FIG. 7 that the strong water line is far removed from the rest of the molecules and does not present a problem, in contrast to infrared measurements. The spectral contribution of each molecule has a unique position, and the line strength can be measured easily. Identification of two molecules of interest is problematic, $N_2O$ and CO, when their concentrations fall into the ppm range. However, both can be identified if adequate resolution can be provided. $N_2O$ has a second Raman active vibrational transition, but it coincides within the assumed 10 $cm^{-1}$ with one of the Fermi pairs in $CO_2$. However, since the low frequency shifted $CO_2$ line is sufficient to determine the $CO_2$ concentrations, the other line, which overlaps the $N_2O$ transition, can be calculated and subtracted from the recorded signal. The difference represents the $N_2O$ contribution. In order to use this approach to measure $N_2O$, the $CO_2$ peaks have to be recorded very precisely. A prior art OMA apparatus could provide the required precision only after heavy lead shielding was applied to remove spurious counts, for instance from cosmic radiation.

The most advanced present Raman spectrometer, which uses an argon ion laser, a multipass cell, and a triple monochromator, as seen in FIG. 2, can achieve a sensitivity level in the ppm range with adequate data collection time. FIG. 8 shows the $CO_2$ spectrum of an air sample produced with a prior art Raman spectrometer. The two strong lines 160, 162 are the Fermi pair at 1285 $cm^{-1}$ and 1388 $cm^{-1}$. The small peak 164 at the 1265.2 $cm^{-1}$ is caused by a hot band; i.e. at room temperature there are a small number of the $CO_2$ molecules in the first vibrational state and they represent an identifiable species. Line 166 at 1370 $cm^{-1}$ is caused by the 1% natural abundance of the $^{13}C$ isotope. Since the $CO_2$ content in air was 0.032%, this line represents the signal of a sample species which is present in the gas beam at the 3 ppm level.

The data collection time required for the prior art spectrometer to provide the spectrogram of FIG. 8 was seven minutes. See J. C. Robinson, et al. Rev. Sci. Instr., Vol. 63, p. 3280–84 (1992). It is desirable to provide an instrument capable of supplying precise, high resolution data in real time, avoiding the lengthy data collection time and the complexity of prior art instruments.

Coherent anti-Stokes Raman spectrometers comprising iodine filters for removal of Rayleigh light are known in the art. See J. W. Nibler, "Coherent Raman Spectroscopy: Techniques and Recent Applications," Applied Laser Spectroscopy, pp. 313–328 (Plenum Press 1990). This type of spectrometer is designed for detection, measurement and study of specific preselected molecular species, and it is not suitable for general analysis because (1) it utilizes multiple laser beams having different frequencies which must impinge upon the target at precise angles (depending on the test being performed) in order to obtain the desired data, and (2) the iodine filter that is used in this reference has too many absorption frequencies, which would interfere with identification of species which may be present in a sample. The iodine filter typically used in such instruments does not have a single, sharp absorption band, but instead has a plurality of such bands, and the instruments are tuned to place the frequency of interest between the bands, and to place the frequency to be removed by the filter at one of the absorption frequencies. For general analysis, it is preferable to employ an apparatus having a fixed geometry and a filter having a single absorption frequency.

The closest known alternate technology to Raman spectroscopy is infrared spectroscopy, such as Fourier transform infrared spectroscopy (FTIS). There are a number of major FTIS products in the prior art. A major shortcoming of infrared spectroscopy is that infrared radiation is unable to interact with some very important molecules in the environment and industry, such as $N_2$, $O_2$, $Cl_2$, and $Br_2$. All of these molecules are Raman active and can be detected by Raman instruments. Another significant disadvantage of infrared spectroscopy is that certain common molecules dominate the spectrum when they are present in the sample. FIG. 9 shows an infrared spectrum of exhaled breath. The spectral range shown spans from 4000 to 300 $cm^{-1}$, and is dominated by the $CO_2$ and $H_2O$ responses. Since these two molecules are strongly infrared active, they block most of the frequencies for other compounds. Therefore, in most infrared spectroscopy applications, $H_2O$ and $CO_2$ have to be removed from the sample before weak impurities can be detected. When the molecules to be measured contain large numbers of atoms, the infrared spectra often becomes so rich that it is almost impossible to analyze. Absolute intensities are also difficult to obtain by infrared methods, because the infrared laser source can alter the population numbers and thus the absorption cross section, which therefore requires pressure dependent measurements and extensive calibrations.

As discussed above, prior art Raman spectroscopy apparatus and methods are deficient because of their complexity and expense, because insufficient resolution is available to rapidly identify the individual contributions of particular molecular species, and because there is no practical, simple, inexpensive way to eliminate the Rayleigh scattered light in order to permit measurement of Raman scattered light at low wave numbers (spectrally close to the Rayleigh frequency). In particular, the prior art does not provide an instrument capable of reliably measuring very small concentrations of molecular species in real time, and that is suitable for use in industrial applications.

SUMMARY OF THE INVENTION

The problems outlined above are in large part solved by the apparatus and methods of the present invention. An instrument has been developed which will significantly extend the present capabilities of Raman spectroscopy. The preferred embodiment of the present invention will greatly improve upon the best prior art instruments, providing data that are several orders of magnitude better in sensitivity and resolution, using a monochromatic diode laser light source, an atomic vapor filter and a Fourier transform spectrometer. The improved Raman spectrometer of this invention will provide high resolution data much more quickly than is possible with prior art spectrometers, permitting real-time analysis of, for example, flue gas or process streams, with a compact, reliable instrument that is suitable for industrial as well as academic use.

Provided that the incident light is highly monochromatic, and provided that the dispersive analyzer (e.g., spectrometer) has sufficient resolution, it is theoretically possible to record hundreds of molecules simultaneously without interference, even when their concentration distribution varies greatly. The present invention provides an analytical instrument which has sufficient simplicity and sensitivity to approach this ideal.

The present invention provides the resolution and precision required to handle the difficult analytic problems presented above, including rapid quantitative analysis of a gas mixture for $N_2O$ and CO, even when their concentrations fall into the ppm range. The present invention also provides substantial improvements over prior art infrared spectroscopy methods, particularly when $CO_2$ and $H_2O$ are present. The Raman spectrum is not overpowered by these common molecules, as is the infrared spectrum, and therefore there is no need to remove them from the sample prior to Raman analysis. In the Raman instrument of the present invention, the incident or scattered frequencies of interest are typically far from any resonance and the sample is optically thin, thus absolute values are easily obtained after the Raman cross sections have been measured on pure samples.

Furthermore, the present invention overcomes the limitations of coherent anti-Stokes Raman spectroscopy, as discussed in the Nibler reference, supra, and provides an apparatus for comprehensive analysis of a sample with an instrument having a fixed geometry and a filter that removes the Rayleigh light without substantially altering or interfering with the Raman spectrum.

The present invention provides an improved Raman spectrometer for analyzing a sample, which may be gaseous, liquid or solid. In one embodiment, the improved spectrometer comprises a conventional dispersive or Fourier transform spectrometer, a substantially single mode light source having a predetermined frequency positioned to illuminate the sample, collection optics to collect light scattered by the sample, and a filter positioned in the path of the collected light for removing light having the predetermined incident frequency. The light source may comprise a plurality of laser diode arrays, which may be optically coupled to a master oscillator in order to regulate the frequency and spectral characteristics of the laser diode arrays.

In a preferred embodiment, a feedback system may be employed in order to assure that the frequency of the light source is identical to the frequency that is absorbed by the filter. This may be done, for example, by directing a beam from the light source through the filter, providing a photodetector to measure how much of the beam passes through the filter, and controlling the frequency of the light source in order to minimize the intensity of the beam detected by the photodetector.

In a preferred embodiment of this improved Raman spectrometer, the filter is a resonant Rayleigh filter that may comprise a glass container filled with a mono-atomic vapor, which may be, for example, a metal (such as alkali) vapor or a noble gas. In an alternate embodiment this filter can be, for example, an ionically doped glass or crystal filter, which can be tuned externally to adjust its absorption characteristics.

A gasdynamic gas focusing system may be used in this invention to provide a gaseous sample in the form of a focused stream.

One aspect of this invention is a filtering system comprising a substantially monochromatic light source for illuminating a sample with light having a predetermined frequency and a resonant Rayleigh filter for absorbing substantially all light at said predetermined frequency while transmitting substantially all other frequencies. This apparatus may be further refined by adding a feedback control system comprising means for directing a beam of light from said light source through the filter, a photodetector positioned to intercept the beam of light after it passes through the filter, and circuitry for controlling the light source in response to a drift signal produced by the photodetector. In presently preferred embodiments, the filter may be a monoatomic gas filter comprising a glass container containing rubidium vapor. Means for heating the filter may be provided to adjust its optical characteristics.

Another aspect of this invention is the monochromatic light source itself, which may comprise a master oscillator for generating a stable master signal at a preselected frequency, and a plurality of laser diode arrays providing light beams that may be directed toward the sample. The laser diode arrays may be optically coupled to the master oscillator, and injection-locked to the preselected frequency of the master oscillator in order to provide a stable, controllable monochromatic light source. The light source may supply light to a multi-pass cell adapted to concentrate and focus the output light from the laser diode arrays onto the sample. The multi-pass cell may comprise a plurality of concave mirrors that receive light from the laser diode arrays and multiply it by reflecting it back and forth numerous times through a focal region where the sample is introduced. The light enhancement in the multi-pass cell can be achieved either by a non-resonant multi-pass configuration as drawn in FIG. 2, or by a resonant cavity configuration ("etalon" mode).

In presently preferred embodiments, an analyzer according to this invention incorporates all of the improvements discussed above, including a plurality of laser diode arrays controlled by a master oscillator, a multi-pass cell, a resonant Rayleigh filter, a feedback control system to ensure that the frequency of the master oscillator corresponds to an absorption band in the filter, and a dispersive or Fourier transform spectrometer to produce a spectrogram of the filtered Raman emissions.

This invention also provides a method for isolating Raman scattered light, comprising illuminating a sample to be tested with substantially monochromatic light having a predetermined frequency, collecting the resulting Rayleigh and Raman emissions, filtering the light to remove Rayleigh emissions by passing it through a resonant Rayleigh filter having an absorption band at said predetermined frequency, and directing the filtered light to an input of a spectrometer, which may be (for example) a Fourier transform spectrometer. The monochromatic light may be generated by a plurality of laser diode arrays, which may be injection-locked by a master oscillator.

In an alternative embodiment of this invention, a Raman instrument is provided for detecting the presence of one or more preselected molecules. This embodiment comprises a monochromatic light source, a multi-pass cell receiving light from the light source and concentrating the light to illuminate a sample, and one or more photodetectors and corresponding filters positioned to detect Raman emissions. In this embodiment, the Raman emissions are not directed to a spectrometer. Instead, each photodetector/filter combination is adapted to detect and measure light having a specific predetermined frequency corresponding to a Raman line generated by a molecule of interest. Each filter is a "notch" or a "band-pass" filter which transmits only the desired Raman line and which absorbs the Rayleigh component and other Raman lines. Alternatively, gratings or other dispersion means may be employed to provide spectral separation, and photodetectors may be positioned to receive the frequencies of interest. This embodiment provides a simplified instrument which is adapted to detect the presence and concentration of a relatively small number of particular molecular species (including atoms or ions).

BRIEF DESCRIPTION OF THE DRAWINGS

So that the manner in which the herein described advantages and features of the present invention, as well as others which will become apparent, are attained and can be understood in detail, more particular description of the invention summarized above may be had by reference to the embodiments thereof which are illustrated in the appended drawings, which drawings form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION OF THE PREFERRED EMBODIMENTS

The Raman spectrometer according to this invention may be adapted to rapidly analyze most any gas mixture or other sample, from the strongest to the weakest component (tens of ppm), on an absolute scale, with a high repetition rate and free of interferences.

Figure 3:
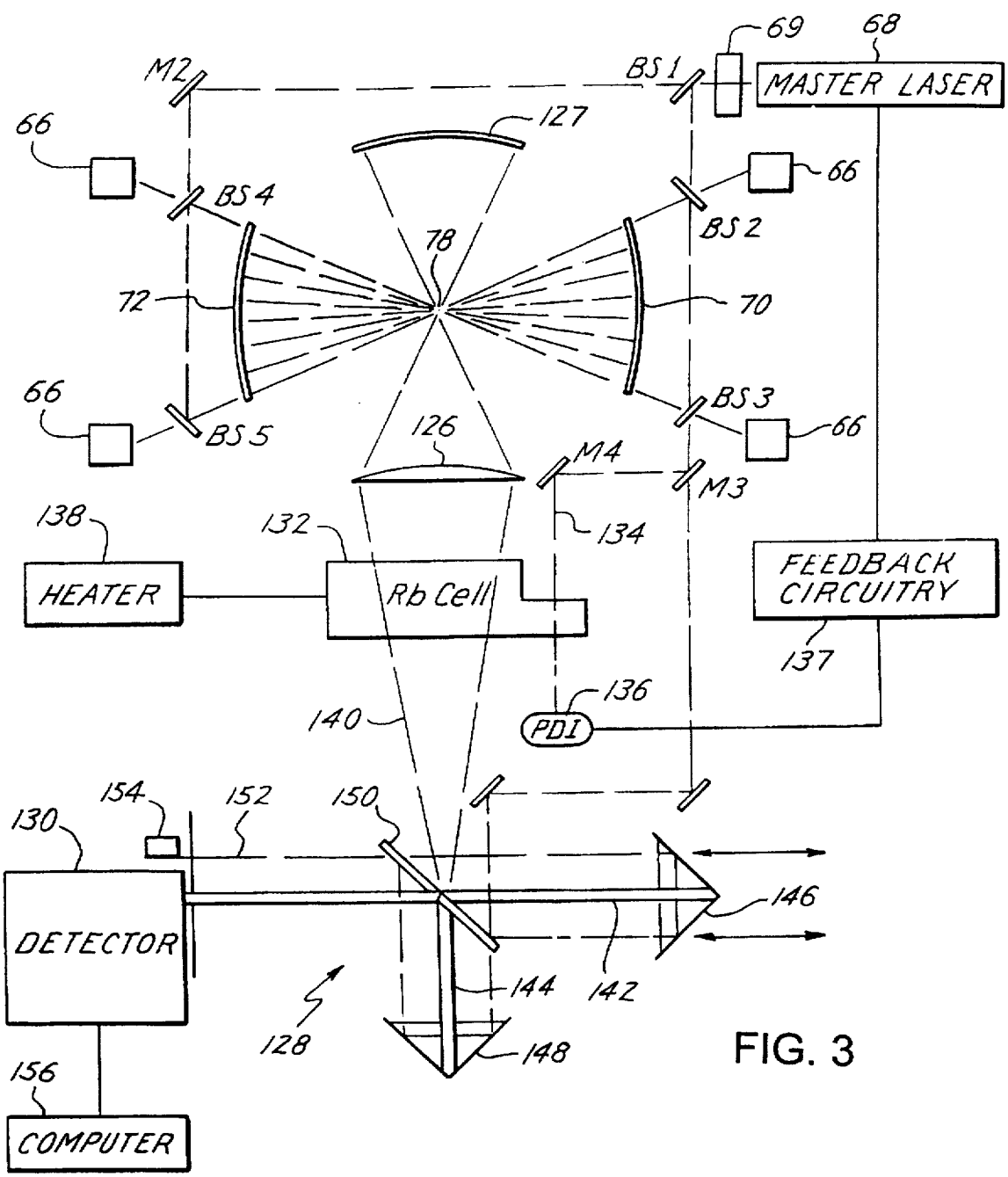
FIG. 3 is a diagrammatic drawing of a Raman spectrometer according to the present invention.

FIG. 3 shows a Raman spectrometer incorporating some of the improvements that constitute this invention. A preferred incident laser source for the present invention includes four one-Watt laser diode arrays 66, which are injection locked by a master oscillator 68. In a preferred embodiment, this oscillator is on resonance with one of the hyperfine transitions of the $D_1$ manifold in rubidium. There are several papers in the literature which report that the high monochromaticity of master oscillator 68 (better than 30 MHz) can be fully transferred to the diode arrays 66 and maintained for any desired length of time. See Wang, et al., *Optics Letters*, Vol. 17, p. 1593 (1992); Yu, et al., *J. Phys III France*, Vol 2, p. 1615–22 (1992). The master oscillator 68 is protected from optical feedback by optical isolator 69. This may be done with an optical isolator based on the Faraday effect in a crystal with a large Verdet constant (available, for example, from Isowave in New Jersey, Model I-80U4). Suitable laser diode arrays 66 are offered by Spectra Diode Labs, San Jose, Calif. (e.g., the SDL-2400 Series). A suitable master oscillator 68 may be a Series SDL-5400, also from Spectra Diode Labs.

The laser diode arrays are made monochromatic by various means, such as injection locking by a single mode master oscillator, by self injection locking in a ring arrangement, by self-injection locking in a grating feedback tuned arrangement or by use as an amplifier of a single mode master laser. (All of these techniques are included when the term "injection-locked" is used herein.)

Figure 4:
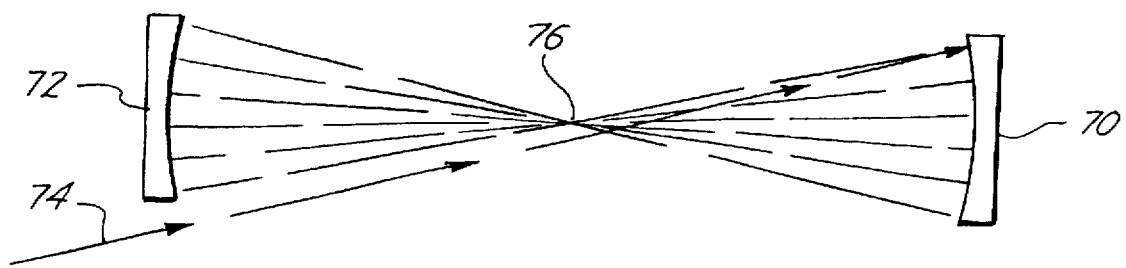
FIG. 4 illustrates the operation of a multi-pass cell that may be used in the present invention.

In a preferred embodiment, diode arrays 66 are mounted at four corners of a special multipass cell comprising mirrors 70 and 72. As seen in FIG. 4, the optics of the reflecting mirrors 70, 72 are so chosen and arranged that they reflect the laser light 74 about 100 times (for example) and form a common focal region 76, where a combined laser power of about 400 W is attained, having the frequency and monochromaticity of the master oscillator. Similar multipass cells have been utilized for some time with single laser beams. See, e.g., J. C. Robinson, et al., *Rev. Sci. Instr.*, Vol. 63, p. 3280–84 (1992). The multipass cell includes two concave mirrors 70, 72 whose focal region 78 is close to half the distance between the mirrors (the focal points of the mirrors are not precisely coincident, and therefore the term "focal region" is used) . Mirrors 70, 72 may be coated with dielectric layers to give reflection coefficients of up to 0.9999. This will minimize the production of stray light and the absorption in the surface, and it will return the laser light substantially unattenuated for the remaining reflections.

Another element of the preferred embodiment is the gas target placed in focal region 78. Most commercial Raman spectrometers have a gas cell that is filled with the gas sample. Appropriate windows are provided in the cell for the incident and scattered light. This arrangement is not suitable for analyzing chemically aggressive substances or molecules which easily coat glass surfaces. Careful light baffles have to be installed to suppress the light scattering from the glass as much as possible, since the scattered light covers the whole spectral range.

Figure 5:
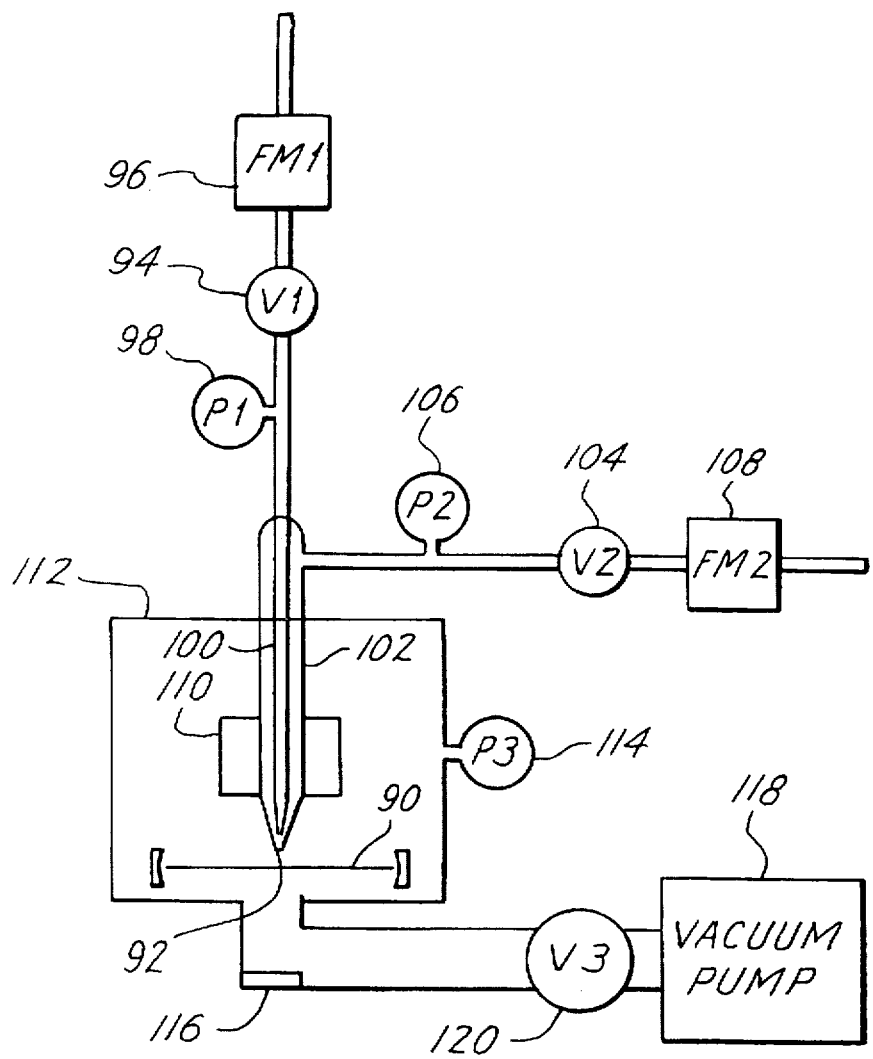
FIG. 5 is an illustration of a sample handling apparatus which can be employed with the present invention.

Referring to FIG. 5, a preferred embodiment of the present invention includes a gasdynamic gas focusing system. This is a sample handling system that includes a double nozzle apparatus that forms an extended, well collimated target by gasdynamic focusing. Other sample handling apparatus, adapted to handle gases (e.g. providing an effusive gas beam), liquid and solid samples, may be used with this invention. Gasdynamic focusing of a gas sample is particularly well suited to this invention because it protects the optical elements of the spectrometer assembly from deterioration due to reactive components in the gas. Furthermore, the gas sample can be heated to ensure that all water present is in vapor form, thereby avoiding solutions that would cause false concentrations to be measured.

Gasdynamic focusing also brings several other advantages. First, there are no sample chamber windows which produce unwanted scattered light. The windows of a prior art sample cell substantially reduce the efficacy of a multipass cell, as some loss occurs each time the laser beam passes through a window. Furthermore, a well-collimated gas beam will never come in contact with the delicate optical surfaces which are in close proximity to the sample. The ability to heat the gas to be studied and to avoid supersonic flow eliminates the need to remove water or any other substance which can solvate or cluster and thus falsify the results.

Gasdynamic focusing was first reported by Keller et al., *Applied Optics*, Vol 23, p. 2146–2151 (1984). See also Muenchausen, et al., *Applied Optics*, Vol. 28, p. 3220–3225 (1989); and J. C. Robinson, et al., *Rev. Sci. Instr.*, Vol. 63, p. 3280–84 (1992) (gasdynamic focusing applied to Raman spectroscopy).

In a preferred embodiment of the present invention, it is desirable to place a gas target such that it is intercepted by laser beam 90 at the focal region of the multi-pass cell illustrated in FIG. 3. The sample gas may be collimated and sheathed in a sheath gas, which is preferably argon (any well characterized gas will suffice). Referring to FIG. 5, gasdynamical focusing is achieved with dual nozzle 92. Interior nozzle 100 supplies the sample gas, the rate of which can be controlled by valve 94. The flow of the sample gas may be measured with flow meter 96 and the pressure of the sample gas above the nozzle may be measured by pressure gauge 98. The sheath gas, which is preferably argon, is introduced into outer nozzle 102 which surrounds inner nozzle 100. The flow of the sheath gas may be controlled by manipulating valve 104, and the pressure and flow of sheath gas may be monitored using pressure gauge 106 and flow meter 108, respectively. A heater 110 may be employed to heat the sample prior to injecting it into the focal region of laser beam 90. A well focused, collimated stream of the sample gas may be generated by this arrangement with appropriate adjustments to the flow rates of the sample gas and the sheath gas and the chamber pressure. Dual nozzle 92 and the multi-pass cell that concentrates laser beam 90 are preferably located inside of vacuum chamber 112, whose vacuum can be monitored using pressure gauge 114. Cold plate 116 is used in a preferred embodiment for condensing any condensable components of the sample gas. The vacuum in vacuum chamber 112 is provided by vacuum pump 118 and the background pressure due to the sheath gas is controlled with valve 120 to optimize the gas dynamic focusing conditions. Through appropriate arrangement of cold plate 116 and the plumbing that couples the vacuum chamber to the vacuum pump, substantially all of the sample gas can be directed immediately out of the vicinity of the multi-pass cell, thus preventing contamination of the multi-pass cell and the collection optics with components of the gas sample, and also preventing condensation on critical optical surfaces. This arrangement provides a well-focused, collimated gas jet that is particularly well suited to real time analysis using the spectrometer of this invention.

In a preferred embodiment, both nozzles 100, 102 are made of quartz to avoid the possibility of organic compounds being catalytically decomposed on the heated walls. Quartz is totally inert to such effects. The sheath gas is preferably argon, which does not contribute to the Raman signals, and its impurity level can be recorded in a calibration run. Spectral analysis of the center of the gas jet shows that the system does not enter supersonic flow. The ratio of Stokes to anti-Stokes lines shows that the temperature of the sample gas jet is close to that of the nozzle, with a Boltzmann distribution in the vibrational and rotational states. The dual nozzle set can be run at any pressure as long as the pressure difference between the center beam, the sheath gas and the reservoir have been chosen properly. An additional benefit of this arrangement is the lack of parasitic scattering from solid surfaces since no glass surfaces are needed to contain the sample, and the multipass focus can be positioned several millimeters below the end of the nozzle 92. This detailed description is provided only to set forth the presently preferred embodiment of the invention. Of course, other sample handling techniques, as are known in the art, may be used with this invention.

Optimized collection optics for the scattered light are known in the art and used in commercial Raman spectrometers. Referring to FIG. 3, in a preferred embodiment an f1 lens 126 and a collecting mirror 127 at ±90° to the incident light collect about 30% of all scattered light and direct it towards the dispersive analyzer 128. Note that all spectral components of the scattered light have the spectral widths of the incident light beam broadened by the Doppler effect in the gas jet. In an effusive gas beam, this can be as much as 1 GHz depending on the molecular weight and the temperature of the sample gas. When it passes through lens 126, more than 99.9% of the scattered light is the elastic or Rayleigh component, having a frequency matching that of master oscillator 68.

The resonant Rayleigh filter 132 of this invention will substantially remove the Rayleigh light without attenuating spectrally proximate Stokes emissions. Referring to FIG. 3, in a preferred embodiment filter 132 includes a glass cell filled with, for example, a mono-atomic vapor, such as rubidium, chosen to have an absorption resonance at the frequency of the Rayleigh scattered light, which is the frequency of the laser diode arrays or other incident light source. At room temperature, this alkali has a vapor pressure of $10^{-6}$ Torr. A 10 cm optical length of rubidium vapor is sufficient to absorb and reduce the Rayleigh light reaching analyzer 128 by up to 10 orders of magnitude. Other atomic vapors can be used in place of rubidium, in combination with suitably chosen laser light sources. For example, another metal vapor or a noble gas may be employed as the filter medium, as well as an ionic doped glass, with a corresponding monochromatic light source chosen to produce a beam at an absorption frequency of the selected filter medium.

In an alternate embodiment, the resonant Rayleigh filter may comprise a resonant optical cavity (etalon) that transmits all of the Rayleigh light while reflecting all of the inelastically scattered Raman light (except for resonant dips at multiples of the cavity's resonant frequency). The Raman light can thus be separated from the Rayleigh light and directed to the input of a spectrometer for analysis. The effective bandwidth of such a resonant optical filter can be adjusted by changing the quality factor of the cavity. In embodiments using a resonant optical cavity, the frequency of the light source of this invention may be locked to the resonant frequency of the cavity by electro-optical or purely optical techniques, as discussed above for use with for example a rubidium filter. For example, see B. Dahmani, et al., "Frequency Stabilization of Semiconductor Lasers by Resonant Optical Feedback," Opt. Lett., 12:11, 876 (1987).

This filtering technique requires that the incident light produced by the diode arrays 66 be substantially on resonance with the absorption frequency of the rubidium cell or other resonant Rayleigh filter. In a preferred embodiment, frequency-matching may be done by locking the master oscillator laser 68 to the filter absorption frequency using a feedback control system. In a preferred embodiment, that control system comprises a portion of the beam from the master oscillating laser 68 directed through rubidium cell filter 132 to impinge upon photodetector 136. If beam 134 from master oscillator 168 is precisely in tune with the absorption frequency of filter 132, a minimum amount of that light will reach photodetector 136. Master oscillator 68 is coupled to photodetector 136 through feedback circuitry 137. Feedback methods well known in the art may be employed to adjust the frequency of master oscillator 68 in response to the amount of light detected by photon detector 136. With a back reflected beam, one can avoid the Doppler width of the rubidium (approximately 500 MHz=0.02 cm$^{-1}$) by producing a Lamb dip, and then only one velocity group will be used in the lock. See A. E. Siegman, Lasers, § 30.6 (University Science Books, Mill Valley, CA, 1986). Precision well below 100 kHz lock frequency has been achieved. Stokes and anti-Stokes light pass through filter 132, suffering some losses only at the inner glass surfaces. The outside glass surface of filter 132 may be coated with a broadband antireflection film.

In addition to the standard, opto-electronic lock-in feedback techniques for control and stabilization of the diode laser frequencies, as described above, other control schemes can be used. For example, an all-optical locking scheme can be used, such as a magnetically induced birefringence feedback locking technique as described in W. D. Lee and J. C. Campbell, "Optically Stabilized Al$_x$Ga$_{1-x}$/GaAs Laser Using Magnetically Induced Birefrigence," Appl. Phys. Lett., 58:10,995 (1991).

If the Doppler broadening of the Rayleigh emissions due to the velocity of the gasdynamic jet or other sample is broader than the room temperature rubidium absorption band, the rubidium absorption band can be readily adjusted by shortening the absorption cell (to control the attenuation of the Rayleigh light, as a small portion is useful for calibration) and operating at higher temperature (to broaden the absorption band) by heating filter 132 with heater 138. These changes maintain the optical density of filter 132 while raising the width of the rubidium absorption line. This filtering technology is stable, simple and inexpensive, and it leaves the light which carries the Raman emission information substantially unchanged. Similarly, in an embodiment where the resonant Rayleigh filter is an ionic doped glass or crystal, the width of the absorption band may be controlled by, for example, controlling the pressure applied to the glass or crystal.

The combination of laser diode arrays 66 injection locked to a precise master oscillator 68 in tune with rubidium absorption cell 132 makes the Raman spectrometer of this invention a superior analytical tool when compared with all instruments currently known.

The Raman scattered light is composed of a series of spectral lines which are shifted from the incident frequency generated by the laser diode arrays 66. Their spectral positions and their intensities provide the information sought which can be analyzed to determine the composition of a sample, the concentration of each component, and other environmental parameters, such as temperature.

The Raman light produced by the apparatus described above may be converted into a spectrogram by any one of a number of known instruments. A preferred instrument for analyzing the Raman light is a Fourier transform spectrometer. FIG. 3 includes an illustration of a Fourier transform spectrometer. It records the spectrum not by the common dispersive devices, such as gratings, prisms, or Fabry-Perot etalons, but by producing an interferogram in the time domain, which can subsequently be converted into a frequency domain spectrogram. An example of such an apparatus is known in optics as a Michelson interferometer. The incident light 140 is divided by a beam splitter 150 into two paths 142, 144, each ending with a mirror, preferably a corner cube 146, 148. Corner cubes reflect incident light parallel to the incident direction, making them particularly useful in a noisy environment. The reflected light passes beam splitter 150 and forms an interference pattern that is recorded at detector 130.

Figure 1:
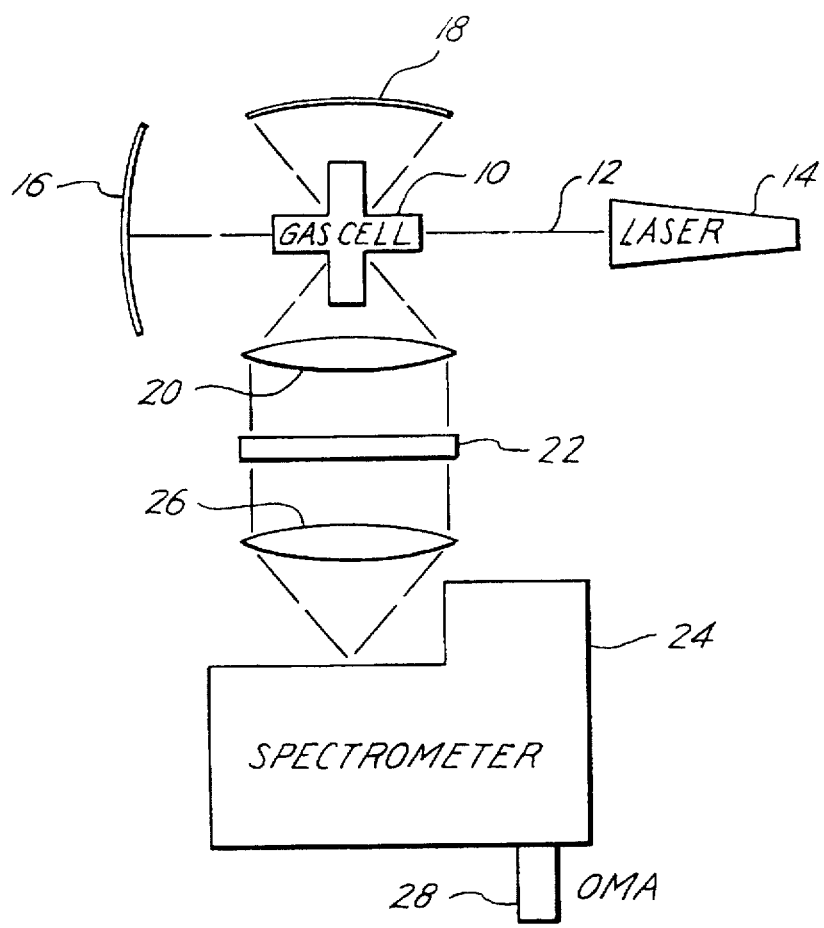
FIG. 1 is a diagrammatic drawing of a generic Raman spectrometer as known in the prior art.
Figure 2:
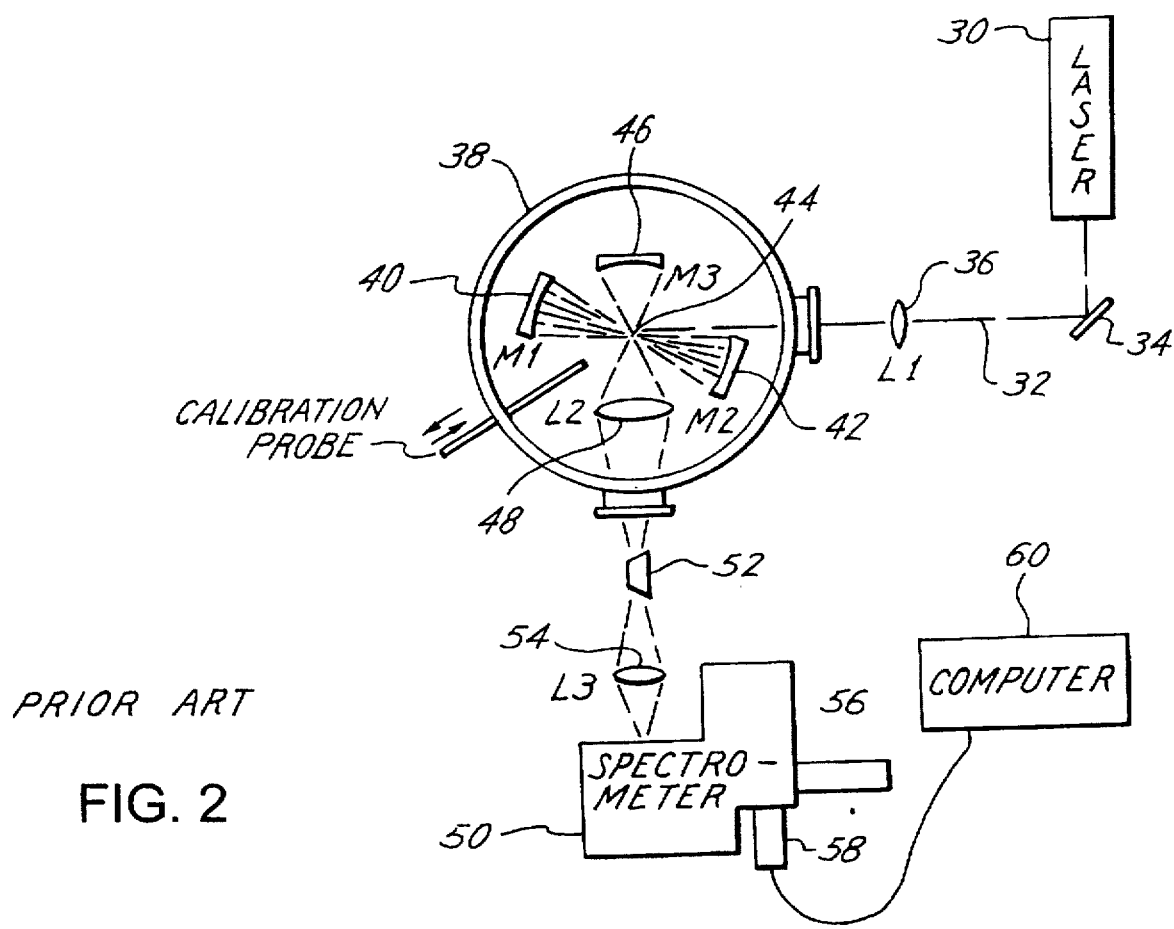
FIG. 2 is also a diagrammatic drawing of a Raman spectrometer as known in the prior art, comprising a multi-pass cell for focusing and intensifying the laser beam.

If the incident light beam 140 is very monochromatic, then the time domain pattern includes a regular series of lines, indicating the pathlength differences in the beams of the two arms of interferometer 128. When one of the mirrors is moved slowly, a sinusoidal pattern is recorded by a stationary detector for every half wavelength the mirror changes its position. The Fourier transform of the intensity pattern will lead to a sharp line which rests on a high frequency background due to the low range cut off. The background will also vary slowly, as the data recording is stopped at the limit of displacement of the mirror. This background will not influence the analysis of the transform since it can be taken into account by theory. The linewidth of the spectral line is a convolution of the light coming off the Raman cell and the resolution of the instrument. For an instrument in which movable corner cube 146 has a large travel distance (in the 10 cm range), the instrumental resolution is not a limiting factor. Each frequency component of the Raman light generates a sinusoidal interferogram, which transforms to a spectral line in the spectrogram. Since all of the collected light arrives at the detector, the signal to noise ratio is large. From this point of view the Fourier instrument records as much light as the OMA in the prior art dispersive instruments illustrated in FIGS. 1 and 2.

Figure 6B:
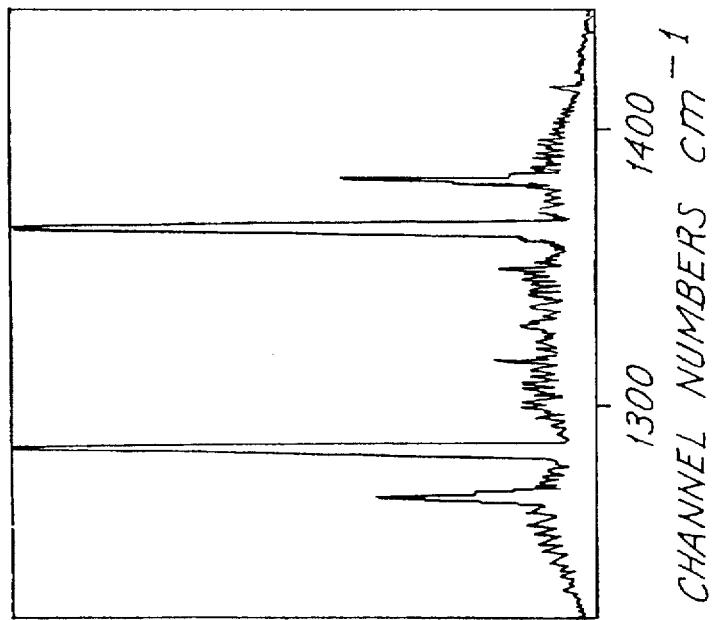
FIG. 6B is a Raman spectrum produced by Fourier transform of the interferogram shown in FIG. 6A.
Figure 6A:
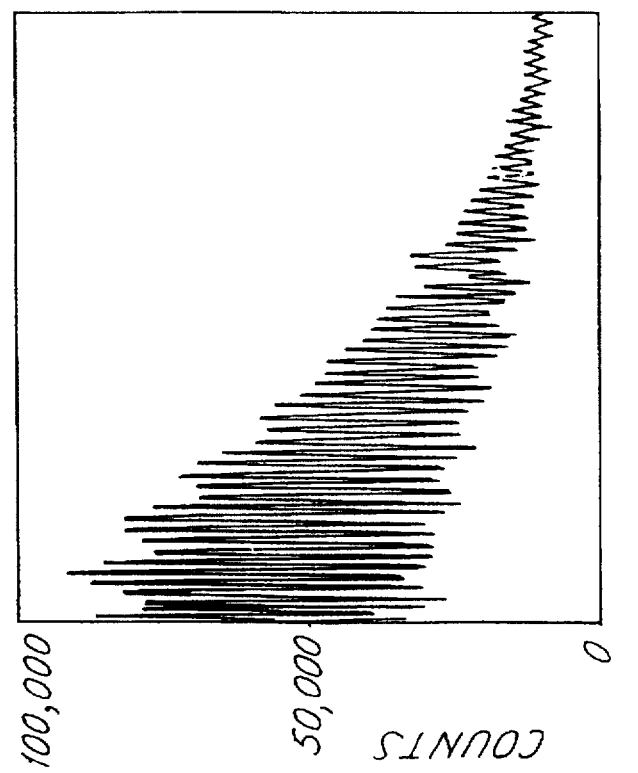
FIG. 6A is an interferogram produced from a $CO_2$ sample.

FIGS. 6A and 6B show a time domain interferogram (6A) and its Fourier transform—the frequency domain spectrogram (6B). In a grating spectrometer, the resolution can only be changed by use of an alternate grating, providing the slit widths are optimized. In the Fourier unit the corner cube travel length, which is easily changed, varies the resolution. Thus, quick, low resolution and slower, high quality spectra can be taken with the same instrument by altering the travel speed and travel length of corner cube 146.

Referring again to FIG. 3, the transformed spectrogram may be calibrated (to determine quantitatively at what wavelength each spectral line appears) by injecting a standard laser beam 152, whose wavelength is very well known, into the spectrometer input. In the prior art a HeNe laser 154 has been used for this purpose. In order to overcome small intensity fluctuations in the injected laser beam, a zero level approach may be chosen that is dependent only on frequency, not on intensity. Every time the derivative of the standard laser intensity crosses zero, the detector records an intensity data point. Note that the HeNe-laser wavelength is only 633 nm, and on a displacement hub of 2.5 cm, a very large amount of data will be recorded. In earlier times, this wealth of data limited the use of the Fourier approach, but today the computer 156 can read and store the gathered information with ease. Obviously, more data and higher precision in intensity recording lead to a superior spectrogram.

Again, the use of laser diodes 66 as standards in the preferred embodiments provides a significant improvement in a Raman spectrometer employing the Fourier transform method. In a preferred embodiment, a 50 mW laser diode 66 can be driven with the use of a constant current, low noise power supply so that its intensity become very stable, up to 1 part in $10^4$. If such a diode is used as a standard in the Fourier unit, one can use fringe splitting techniques and take data at an even higher rate.

In the preferred embodiment, the spectrogram derived by transforming the interferogram represents the whole spectral range, from 0.01 cm$^{-1}$ to more than 5000 cm$^{-1}$ from the Rayleigh line.

A suitable Fourier transform spectrometer for use in this invention can be obtained from Mattson Instruments (Model RS 10500), Madison, Wis.

The Fourier transform spectrometer instrument described so far is based on a standard Michelson interferometer. Alternatively, a Fourier transform spectrometer based on a folded beam path may be employed, which gives even greater resolution because the pathlength difference is doubled. See J. L. Hall and S. E. Lee, Applied Phys. Lett., Vol. 29, p. 367 et seq. (1976).

Due to the use of ultra monochromatic diode laser arrays and removal of the Rayleigh light by atomic absorption, preferred embodiments of this invention can provide spectral resolutions of 0.02 cm$^{-1}$. This permits identification of a molecular species in the presence of hundreds of others because the spectral lines may be resolved without overlap. In an optimized embodiment, this invention will permit resolution between organic compounds which differ only in one isotope.

As outlined above, the Raman spectrometer unit according to this invention will provide vast improvements over presently available units, including those already employing the Fourier transform method, in several aspects. Due to the use of injection-locked laser diodes, the scattered light will consist of a series of spectral lines which are very narrow, including the very strong Rayleigh component. Since, in the presently preferred embodiment, the lasers operate at the $D_1$ transition of rubidium, a rubidium absorption cell in front of the spectrometer will substantially eliminate the elastically scattered Rayleigh light. This invention, embodied in an inexpensive and commercially practical apparatus, avoids the crippling effects of the Rayleigh component, which covers the entire interferogram, and thus permits detection of Raman light at much smaller Raman shifts (i.e., closer to the Rayleigh line) and provides a better signal to noise ratio over the entire spectrum than possible with prior art apparatus. Since all the Stokes and anti-Stokes lines have the same line width as the incident light from the laser diode arrays (plus Doppler broadening), they will not overlap if suitable resolution is attained through proper selection of components. A complex, unknown mixture can be analyzed without interferences because this invention makes it possible to resolve and identify each spectral line.

Raman spectrometers according to this invention will extend the spectral range to very low frequency rotational and vibrational excitations, because it allows measurements in the spectral region very close to the Rayleigh line. This is important for many research and industrial applications, such as solid state physics (e.g., magnetically dilute semiconductors), polymers, biology (e.g., dome modes in hemoglobin), and particulate analysis.

While the above discussions have focused primarily on analysis of gases, this is no fundamental limitation. The instrument can analyze the spectra from impurities in solutions and from surfaces as well (including surfaces coated with adsorbates), with properly prepared and positioned samples, and appropriate optical elements. In general, the strong interaction with the environment in these cases will broaden the spectral lines, and the resolving power of the Fourier analyzer would generally not be beneficial. If, however, the concentrations of the substances under investigation are low enough and the required sampling rate high enough, a Fourier transform instrument according to this invention might still be the tool of choice due to its superior sensitivity. In any event, the Rayleigh filter and corresponding resonant light source of this invention may be used beneficially with any dispersive spectrometer with OMA or Fourier transform spectrometer to eliminate the Rayleigh line and provide for resolution of Raman lines at low wave numbers. This invention is thus well suited for liquid analysis applications including real time monitoring of drinking water supplies and impurity monitoring in chemical process streams at ppm sensitivity levels.

An important application for the technology of this invention will be in an instrument for continuous emission monitoring (CEM) of waste gases (e.g. smokestack or exhaust monitoring). Gases are emitted into the environment in many situations in science, industry and medicine, including exhaust gases from power plants as well as gases escaping into the atmosphere from present and former waste disposal activities. Impurities are present in the air in dwellings such as mobile homes and family residences. In industry, CEM is very important to guarantee the safety of the work force and the public, and real-time, on-line monitoring can be a powerful tool for production controls.

Furthermore, instruments incorporating the present invention will be useful in medical applications. For example, it is desirable in surgery to monitor the oxygen content of a patient's exhaled breath as a function of time. Physicians would like to have an on-line instrument with a temporal resolution of 100 msec to see the onset, plateau and backslope of a single breath stroke. A simple instrument embodying the present invention would fill this need. It would not only tell the surgeon the $O_2$ distribution, but also the $CO_2$ and $H_2O$ concentrations, as well as the presence of other substances of interest, such as anesthetic gases.

The following example will focus on one particular application of a Raman instrument according to this invention, for which it is extremely well suited: the smoke stack "sniffer." The present invention is particularly well suited for quickly analyzing a flue gas mixture because it can record the components of strongly differing concentrations and large temporal variations without interferences.

Figure 7:
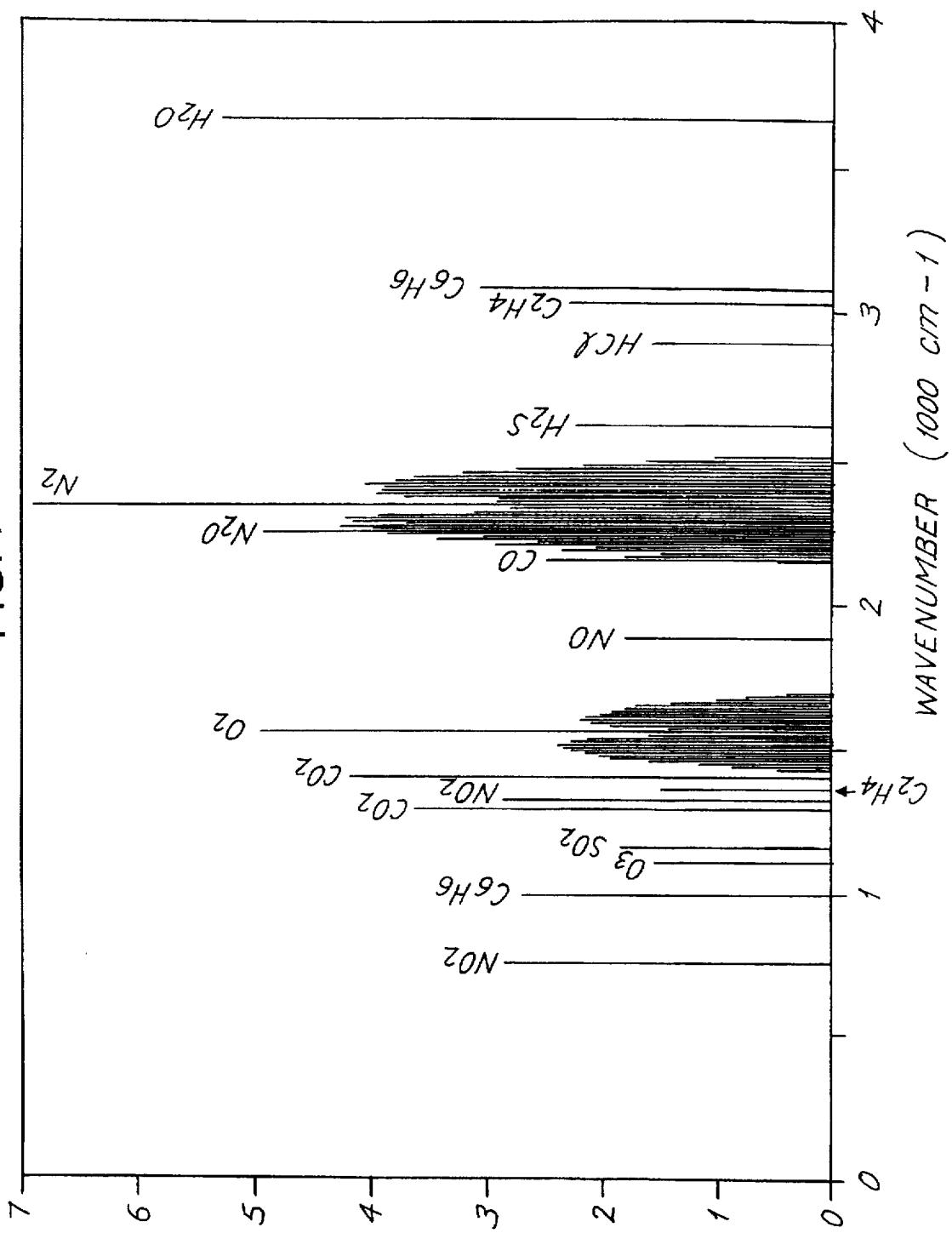
FIG. 7 is a calculated Raman spectrum of a hypothetical gas mixture.
Figure 8:
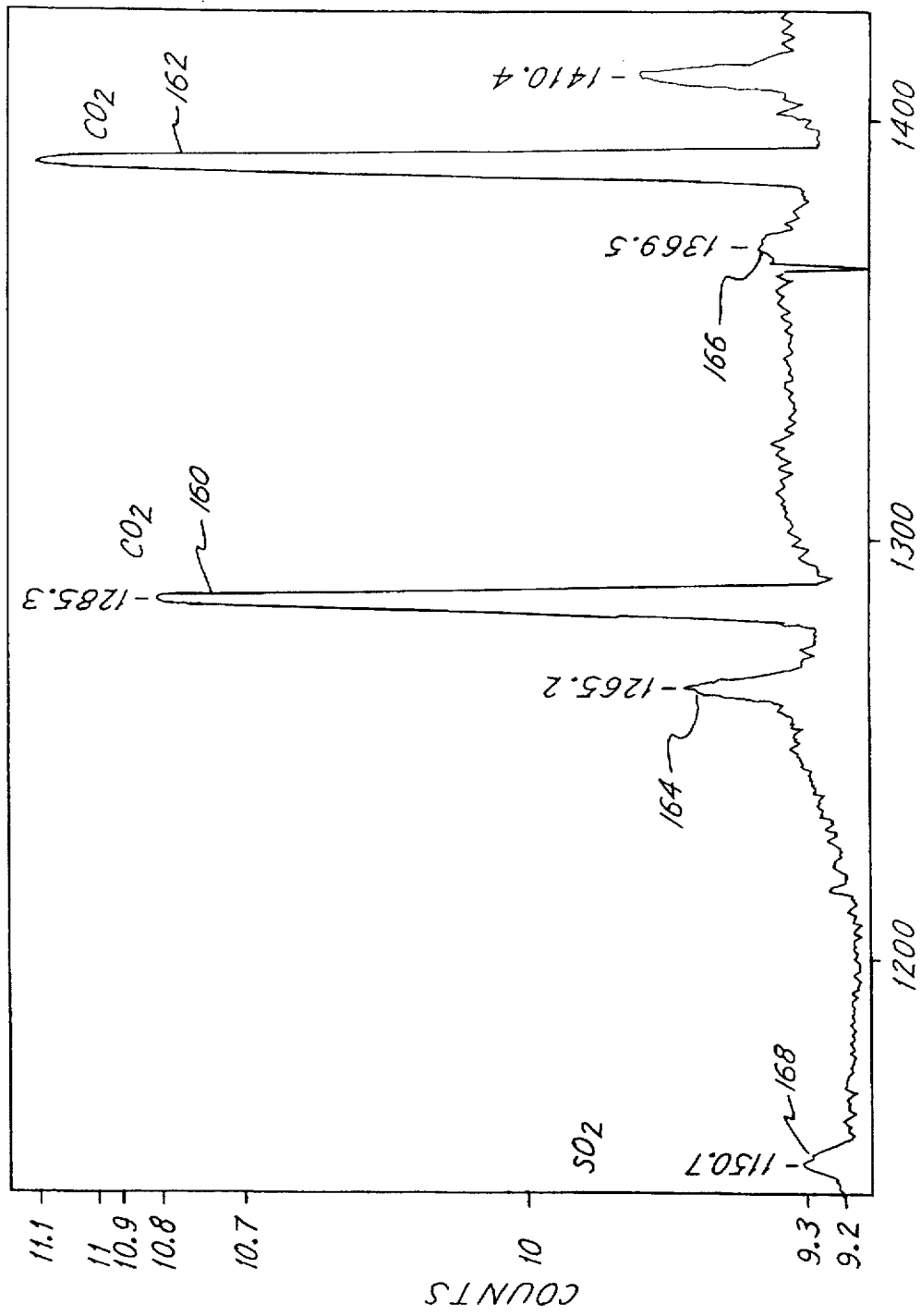
FIG. 8 is a Raman spectrum of an air sample, produced by a prior art instrument, showing the $CO_2$ Fermi pair.
Figure 9:
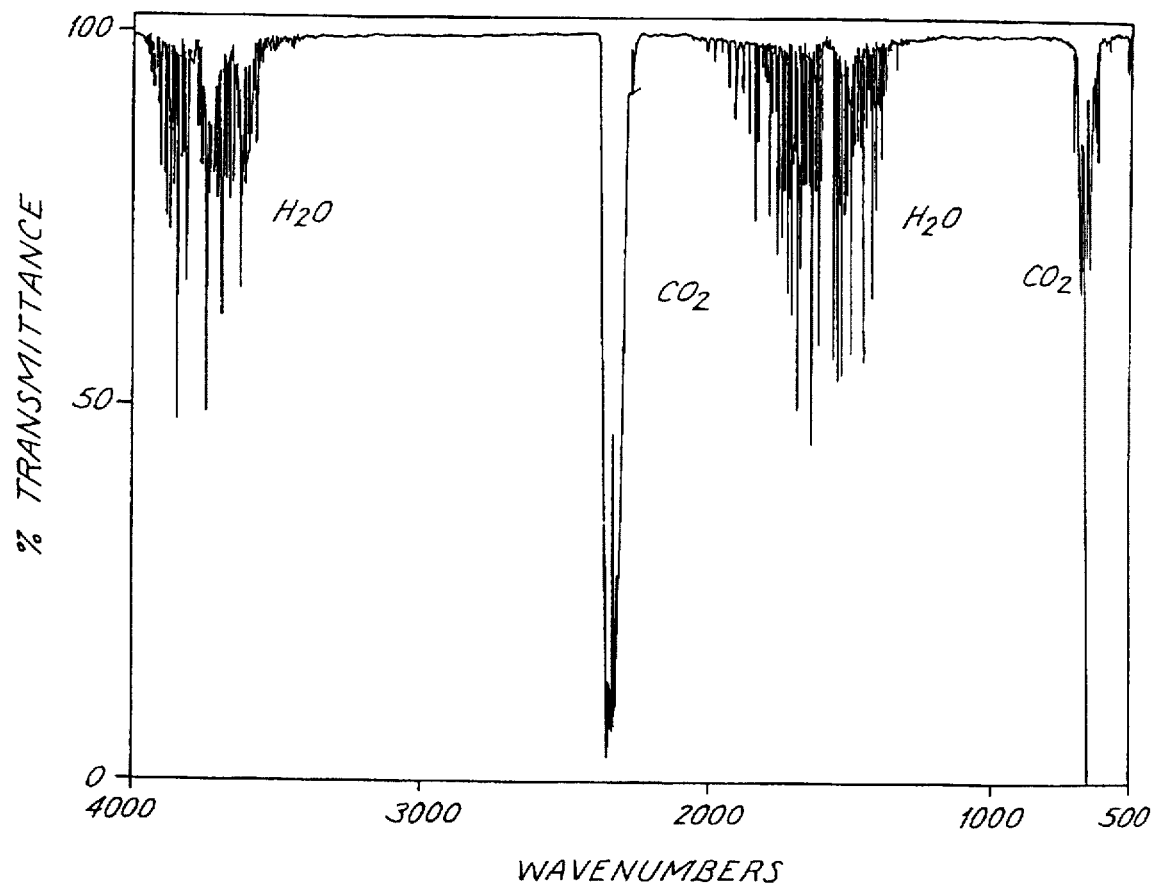
FIG. 9 is a prior art infrared spectrum of exhaled breath, showing the dominating effect of the $CO_2$ and $H_2O$ responses.

There are four major constituents in conventional smoke stack exhausts: $N_2$, $O_2$, $CO_2$, and $H_2O$. Two of these gases, $CO_2$ and $H_2O$ make monitoring the mixtures impossible with IR-spectroscopy since they block the major part of the spectral range as shown in FIG. 9. A Raman spectrometer will find the water line all alone at the high frequency end of the spectrum, without other peaks nearby, as shown in FIG. 7. Smoke stack molecules such as $CO_2$, $O_3$, $C_6H_6$, give strong signals and are readily recorded. Techniques are known in the art for resolving other molecules of interest.

A Raman spectrometer embodying the present invention is useful for quality control of ultra pure gases used in the semiconductor industry. A high degree of purity has to be maintained all the way to the reactor vessels and process equipment. Whenever something goes wrong within a semiconductor wafer processing operation, the purity of the gases used must be verified. As impurities in the part per billion range can be detrimental, these measurements are not trivial. The only known method currently available for providing the required resolution is use of a triple tandemed mass spectrometer. Such instruments are very expensive and require a very experienced operator, since extensive calibrations are needed to tame a finicky quadrupole mass spectrometer. A Raman unit according to this invention provides an efficient instrument for obtaining the required measurements.

Figure 10:
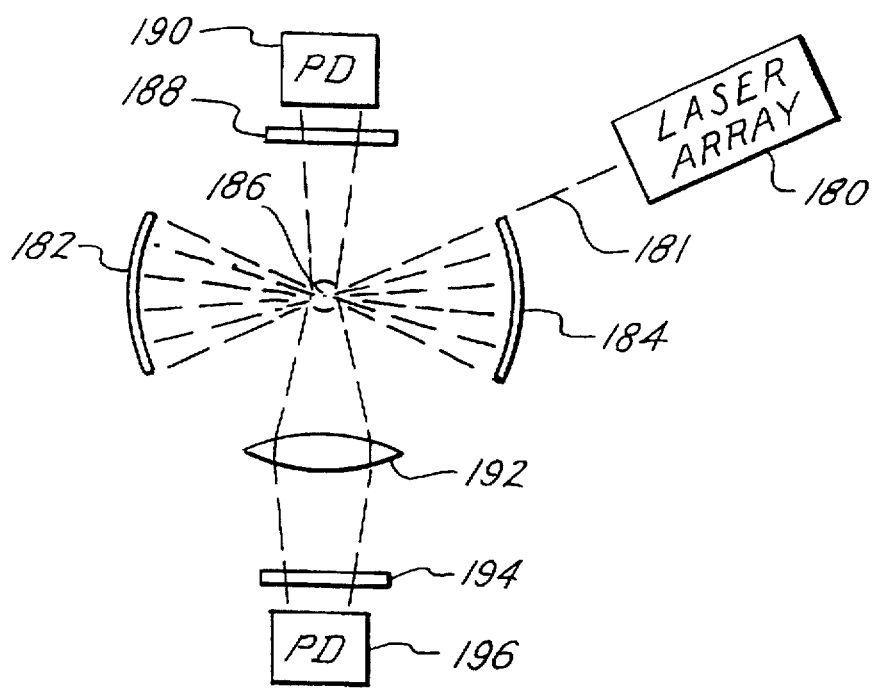
FIG. 10 is a diagrammatic drawing of an alternate embodiment of the present invention.

In yet another embodiment of the present invention, a highly monochromatic light source, for example a laser diode array, is employed to detect and measure the concentration of preselected molecular species (including atoms and ions) in a sample. This is a simplified version of the invention, because it is intended only for detecting specific, preselected Raman lines that occur spectrally distant from the Rayleigh line. Referring to FIG. 10, one or more laser diode arrays 180 are used to provide a light beam 181 directed into a multipass cell comprising mirrors 182, 184.

As discussed above, the multipass cell multiplies the light beam in the common focal region of mirrors 182, 184, where sample 186 is introduced. When sample 186 is excited by the incident light, Rayleigh and Raman emissions are scattered in all directions. Some of these emissions impinge upon filter 188, which is chosen to transmit only light having a specific, preselected frequency, corresponding to a Raman line generated by a molecule whose presence is to be detected. The light at said preselected frequency reaches photodetector 190, where it is detected and an output signal is generated. Substantially all of the Rayleigh light, as well as Raman light at non-selected frequencies, is absorbed by filter 188. If desired, suitable optical collecting elements, such as lens 192, may be employed as shown to direct scattered light toward filter 194 and photodetector 196. If it is desired to detect or measure a plurality of selected molecules (or selected Raman lines) that may occur in a sample, a corresponding plurality of filters and associated photodetectors may be positioned around the sample, each filter selected to transmit one of the Raman lines of interest to its corresponding photodetector. This type of simplified Raman instrument is useful in surgery, where it may be adapted, for example, to provide precise, real-time measurements of $H_2O$, $CO_2$, and $O_2$ concentrations in a patient's breath. Alternatively, it may be adapted to measure concentrations of one or more selected toxins, impurities, or other substances in the environment or in a process stream.

Further modifications and alternative embodiments of this invention will be apparent to those skilled in the art in view of this description. Accordingly, this description is to be construed as illustrative only and is for the purpose of teaching a person skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

We claim:

1. An improved Raman spectrometer for analyzing a sample, comprising:

a spectrometer for producing a spectrogram of light directed into an entrance of said spectrometer;

a plurality of substantially monochromatic light sources having a predetermined frequency, the light sources reflecting multiple times in a multipass cell and positioned to illuminate said sample placed in a target region;

collection optics for collecting light scattered by the sample when the sample is illuminated by said monochromatic light sources, and for directing a collected light beam to the entrance of the spectrometer; and a filter positioned in the path of the collected light beam for removing light having said predetermined frequency from the collected light beam, the filter comprising a single line removal filter including a monoatomic vapor that has a single narrow absorption band at the Rayleigh frequency and that transmits substantially all other frequencies in the Stokes and anti-Stokes regions.

2. The improved Raman spectrometer of claim 1, wherein the light sources comprise a plurality of injection-locked laser diode arrays.

3. The improved Raman spectrometer of claim 2, wherein the light sources further comprise a master oscillator optically coupled to the laser diode arrays and to the filter to regulate the frequency of the light sources.

4. The improved Raman spectrometer of claim 3, further comprising a feedback control system coupled to the filter and to the master oscillator for maintaining the frequency of the light sources at the predetermined frequency, the feedback control system comprising optical elements to direct a beam of light from the master oscillator through the filter; a photodetector positioned to detect said beam of light after passing through the filter; and feedback circuitry for controlling the frequency of the light [source] sources in response to a signal produced by said photodetector.

5. The improved Raman spectrometer of claim 1, wherein the single line removal filter comprises a mono-atomic alkali vapor.

6. The improved Raman spectrometer of claim 1, further comprising a gasdynamic gas focusing system for placing a focused stream of a gaseous sample in said target area.

7. The improved Raman spectrometer of claim 1, wherein the spectrometer is a Fourier transform spectrometer.

8. The improved Raman spectrometer of claim 1, wherein the target region is free from any light scattering surface excluding a surface of the sample.

9. The improved Raman spectrometer of claim 1, wherein the spectrometer is configured to perform real-time continuous emission monitoring.

10. The improved Raman spectrometer of claim 6, wherein the gas focusing system prevents the focused stream from contacting optical surfaces of the spectrometer.

11. The improved Raman spectrometer of claim 6, wherein the gas focusing system includes a heater adapted to vaporize water in the sample.

12. The improved Raman spectrometer of claim 6, wherein the gas focusing system includes a cold plate.

13. The improved Raman spectrometer of claim 7, wherein the Fourier transform spectrometer includes a Michelson interferometer.

14. The improved Raman spectrometer of claim 13, wherein the Fourier transform spectrometer includes a corner cube having a variable travel length and variable travel speed for varying a resolution and a time required for the spectrometer to produce the spectrogram.

15. An improved Raman spectrometer for producing a Raman spectrograph of a selected target sample, comprising:
a spectrometer;
means for producing substantially monochromatic light from a plurality of laser diode arrays, said light reflected multiple times in a multipass cell to form a focal region, said light having a predetermined frequency for illuminating said target sample, said light adapted to cause Raman emissions from said sample;
means for collecting light scattered from said sample when said sample is illuminated by said monochromatic light and forming said scattered light into a beam, and means for directing said beam to said spectrometer;
means for filtering said beam to remove substantially all light having said predetermined frequency and to transmit substantially all other light, said filtering means comprising a mono-atomic vapor having an absorption band at said predetermined frequency disposed in the path of said beam before it reaches said spectrometer;
means for tuning said predetermined frequency of said monochromatic light to coincide with said absorption band; and
means for analyzing said beam after it reaches said spectrometer to produce said spectrograph.

16. The improved Raman spectrometer of claim 15, wherein the means for filtering include an ionic doped glass.

17. The improved Raman spectrometer of claim 15, wherein the spectrometer is configured to perform real-time continuous emission monitoring.

18. A Raman spectroscopy apparatus for analyzing a sample, comprising:
a plurality of injection-locked light sources for producing monochromatic light locked at a predetermined frequency;
a multipass cell for reflecting the monochromatic light multiple times to form a focal region;
collection optics for collecting scattered light from a sample in the focal region and for directing the scattered light away from the sample;
a mono-atomic vapor single line removal filter for absorbing light having the predetermined frequency from the scattered light and for transmitting all other light in Stokes and anti-Stokes regions;
a feedback control system coupled to the filter for maintaining the predetermined frequency of the monochromatic light; and
a spectrometer optically coupled to the filter for producing a spectrogram of light transmitted through the filter directed to an entrance of the spectrometer.

19. The apparatus of claim 18, wherein the apparatus is configured to perform real-time monitoring of liquids or gases.

20. The apparatus of claim 18, wherein the apparatus is configured to monitor exhaled breath as a function of time with a temporal resolution of approximately 100 milliseconds.

21. A Raman spectroscopy apparatus for performing real-time continuous emission monitoring of a sample, comprising:
a gasdynamic gas focusing system for delivering a focused stream of the sample into a target region;
a plurality of injection-locked laser diode arrays for producing monochromatic light locked at a predetermined frequency;
a master oscillator optically coupled to the laser diode arrays, the master oscillator locking the monochromatic light at the predetermined frequency;
a multipass cell for reflecting the monochromatic light multiple times to form a focal region, wherein the focal region overlaps the target region;
collection optics for collecting scattered light from the sample and for directing the scattered light from the target region;
a mono-atomic vapor single line removal filter having an absorption band corresponding to a Rayleigh frequency, the filter absorbing the scattered light directed from the target region having the predetermined frequency and transmitting substantially all other light in Stokes and anti-Stokes regions;
a feedback control system coupled to the filter and to the master oscillator, the feedback control system maintaining the predetermined frequency of the monochromatic light; and
a spectrometer optically coupled to the filter for producing a spectrogram of light transmitted through the filter directed to an entrance of the spectrometer, the spectrogram including emission monitoring information.

22. The apparatus of claim 21, wherein said target area is free from any light scattering surface excluding a surface of the sample.

23. The apparatus of claim 21, further comprising a heater coupled to the gas focusing system.

24. The apparatus of claim 21, wherein the feedback control system comprises: optical elements to direct a beam of light from the master oscillator through the filter; a photodetector positioned to detect the beam of light after it passes through the filter; and feedback circuitry for controlling the master oscillator in response to a drift signal produced by the photodetector.

25. The apparatus of claim 21, further comprising an optical isolator coupled to the master oscillator.

26. The apparatus of claim 21, wherein the plurality of injection-locked laser diode arrays consists of four injection-locked laser diode arrays mounted at four corners of the multipass cell.

27. The apparatus of claim 21, wherein the multipass cell reflects the monochromatic light approximately 100 times.

28. The apparatus of claim 21, wherein the filter comprises rubidium.

29. The apparatus of claim 28, wherein the predetermined frequency corresponds to a hyperfine transition frequency of rubidium.

30. The apparatus of claim 21, further comprising a heater coupled to the filter.

31. The apparatus of claim 21, wherein the spectrometer is a Fourier transform spectrometer.

32. The apparatus of claim 31, wherein the Fourier transform spectrometer includes a Michelson interferometer including a corner cube having a variable travel length and a variable travel speed for varying a resolution and a time required for the spectrometer to produce the spectrogram.

* * * * *

UNITED STATES PATENT AND TRADEMARK OFFICE
CERTIFICATE OF CORRECTION

PATENT NO. : 5,786,893

DATED : July 28, 1998

INVENTOR(S) : Manfred F. Fink, John C. Robinson and Walter F. Buell

It is certified that error appears in the above-identified patent and that said Letters Patent is hereby corrected as shown below:

In claim 4, column 17, line 13, delete"[source]".
In claim 14, column 17, line 42, delete "comer" and insert --corner-- therefor..

Signed and Sealed this

Twentieth Day of October, 1998

Attest:

BRUCE LEHMAN

*Attesting Officer*   *Commissioner of Patents and Trademarks*